(12) United States Patent
Cantu et al.

(10) Patent No.: US 7,426,260 B2
(45) Date of Patent: Sep. 16, 2008

(54) POLYCHRONIC DIGITAL RADIOGRAPHY DETECTOR WITH PATTERNED MASK FOR SINGLE-EXPOSURE ENERGY-SENSITIVE X-RAY IMAGING

(75) Inventors: Gary R. Cantu, San Carlos, CA (US); Brian P. Wilfley, Los Altos, CA (US); Joseph A. Heanue, Palo Alto, CA (US)

(73) Assignee: Eklin Medical Systems, Inc., Santa Clara, CA (US)

( * ) Notice: Subject to any disclaimer, the term of this patent is extended or adjusted under 35 U.S.C. 154(b) by 0 days.

(21) Appl. No.: 11/250,867

(22) Filed: Oct. 14, 2005

(65) Prior Publication Data

US 2006/0227933 A1 Oct. 12, 2006

Related U.S. Application Data

(60) Provisional application No. 60/665,402, filed on Mar. 25, 2005, provisional application No. 60/619,315, filed on Oct. 14, 2004.

(51) Int. Cl.
*G21K 3/00* (2006.01)
(52) U.S. Cl. .................. 378/98.8; 378/156; 378/20; 250/370.11
(58) Field of Classification Search ............ 378/62, 378/2–3, 20, 98.8, 156–159; 250/370.11, 250/390.11, 370.09
See application file for complete search history.

(56) References Cited

U.S. PATENT DOCUMENTS

| 4,029,963 | A |   | 6/1977  | Alvarez et al. |
|-----------|---|---|---------|----------------|
| 4,413,353 | A | * | 11/1983 | Macovski et al. ............. 378/62 |
| 4,933,562 | A | * | 6/1990  | Roziere ...................... 250/367 |
| 4,963,746 | A | * | 10/1990 | Morgan et al. ......... 250/363.02 |
| 5,329,124 | A | * | 7/1994  | Yamamoto et al. .......... 250/367 |
| 5,451,793 | A |   | 9/1995  | Boone |
| 6,332,015 | B1| * | 12/2001 | Honda ..................... 378/98.11 |
| 2005/0084073 | A1 | * | 4/2005 | Seppi et al. ................ 378/156 |

OTHER PUBLICATIONS

J. Boone, PhD., "Binary Screen Detector System for Single-Pulse Dual-Energy Radiography" *Radiology*, (1992) 183:863-70.
David L. Gilblom, et al., "Operation and Performance of a Color Image Sensor with Layered Photodiodes," *Proceedings of the SPIE*, vol. 5074, 2003.

\* cited by examiner

*Primary Examiner*—Hoon Song
(74) *Attorney, Agent, or Firm*—Gordon & Rees LLP

(57) ABSTRACT

A digital radiography system, having: a pixilated optical detector; and a mask positioned adjacent to the pixilated optical detector, the mask comprising a repeating pattern of first and second portions configured to pass different wavelengths of electromagnetic radiation therethrough such that a polychromic X-ray image can be taken using only a single X-ray exposure with a single imaging detector.

19 Claims, 8 Drawing Sheets

POLYCHRONIC DIGITAL RADIOGRAPHY DETECTOR WITH PATTERNED MASK FOR SINGLE-EXPOSURE ENERGY-SENSITIVE X-RAY IMAGING

RELATED APPLICATIONS

The present application claims the benefit of U.S. Provisional Patent Application No. 60/619,315, entitled "Polychronic Digital Radiography Detector with Patterned Mask Superimposted Thereon", filed Oct. 14, 2004 and claims the benefit of U.S. Provisional Patent Application No. 60/665,402, entitled "Method and Apparatus for Single-Exposure Energy-Sensitive X-Ray Imaging" filed Mar. 25, 2005. Both U.S. Provisional Patent Applications 60/619,315 and 60/665,402 are hereby incorporated herein by reference in their entirety.

TECHNICAL FIELD

The present application relates to digital radiography systems.

BACKGROUND OF THE INVENTION

Taking X-ray images of a patient at different wavelengths of light is very useful since different body features are highlighted at different wavelengths of light.

The process of compiling radiographic images of a patient at different wavelengths of light is commonly referred to as "polychromic" X-ray imaging.

Existing systems for taking polychromic X-ray images typically involve first imaging the patient with a first X-ray beam at a first wavelength of light, and then first imaging the patient with a second X-ray beam at a second wavelength of light.

A disadvantage of this approach is that the beam emitter used must be configured to selectively emit an X-ray beam at (at least) two different wavelengths. Moreover, another disadvantage is that the patient is exposed to two different X-rays, one after another. For health reasons, it is always desirable to limit the number of X-ray exposures to the patient. An additional disadvantage is that the two X-rays are recorded at different times (during which time the patient may have moved).

In other existing systems, at least two stacked X-ray-sensitive detectors are used. The first detector is preferentially sensitive to low-energy X-rays, is partially transparent to higher-energy X-rays, and is located between the object being imaged and the second detector. The second detector is preferentially sensitive to high-energy X-rays. Both layers are exposed using a single exposure from the X-ray beam. This so-called "single-exposure, dual-detector" technique overcomes the motion mis-registration problem of the dual-exposure technique.

For example, an X-ray-sensitive detector may be used that includes an X-ray-sensitive scintillator layer to convert each incident X-ray photon into numerous optical (visible) photons. The X-ray sensitive scintillator layer is coupled to a light-sensitive detector in order to make a recording (image) of the incident X-ray photons. For a "single-exposure, dual-detector" technique, at least two light-sensitive detectors are therefore required. This represents a burden of complexity and expense.

U.S. Pat. No. 4,029,963 to Alvarez discloses a method of recording X-ray images with energy sensitivity wherein two stacked X-ray-sensitive layers are constructed of distinct scintillator materials such that the first layer (preferentially sensitive to low X-ray energies) generates optical photons of a first color, and the second layer (preferentially sensitive to high X-ray energies) generates optical photons of a second, substantially different color. These two scintillator layers are optically coupled to a single color-sensitive photographic film located between the two scintillator layers with the result that the optical signals from the two X-ray sensitive layers are recorded as different colors on the single color film. This method has the disadvantages that the film must be developed, and that if further processing of the images is desired, for example to produce derived images of either bone or soft tissue, the image on the film must be digitized.

U.S. Pat. Nos. 5,216,252; and 5,451,793 and the system described in Radiology (June 1992; 183(3):863-70) by Boone describe a binary screen detector system for single-pulse dual-energy radiography, and a method for single-exposure (called by them "single-pulse") energy-sensitive X-ray imaging involving a single X-ray-sensitive layer, wherein the X-ray-sensitive layer (called by them a "binary screen") comprises a mixture of two scintillator materials. As in the above Alvarez system, described above, the scintillator materials are chosen such that one scintillator material is preferentially sensitive to low-energy X-rays and generates optical photons of a first color (first wavelength), and another scintillator material is preferentially sensitive to high-energy photons and generates optical photons of a second color (second wavelength.) In this system, the two scintillator materials are mixed to form a single scintillator layer. The single layer is simultaneously viewed by two different optical cameras, the first camera having an optical filter that makes it sensitive to the optical emission of the low-energy scintillator, and the second having an optical filter that makes it sensitive to the optical emission of the high-energy scintillator. This system has the advantages that only a single exposure (pulse) is required, and that the cameras can be electronic thereby providing immediately images that can be further processed by computer.

Unfortunately, a disadvantage of this system is that, due to the finite size (small numerical aperture) of the feasible coupling lenses required to form images of the optical emissions of the X-ray sensitive layer on the respective optical detectors, a large fraction of the optical photons generated by X-ray-sensitive layer are not received by the optical detectors and are therefore lost. As stated by the inventors, this results in an optical "quantum sink" with the effect that the system is not as efficient in recording incident X-rays as desired, that is, that the system has a low detective quantum efficiency (DQE.)

What is instead desired is a simple system in which a polychromic X-ray image can be generated from a single X-ray beam imaging the patient. It is also desirable that such system does not require two separate camera systems. It is also desirable that such image be acquired in a digital format.

SUMMARY OF THE INVENTION

The present invention provides a digital radiography system, having: a pixilated optical detector; and a mask positioned adjacent to the pixilated optical detector, the mask comprising a repeating pattern of first and second portions configured to pass different wavelengths of electromagnetic radiation therethrough.

In one embodiment, first and second portions of the mask are configured to pass different wavelengths of X-rays therethrough. In other embodiments, the first and second portions of the mask are configured to pass different wavelengths of visible light therethrough. The repeating pattern of first and second portions may be formed as a grid across the front of the optical detector. In optional embodiments, a repeating pattern of third portions passing other different wavelengths of radiation therethrough may also be included. Thus, the present invention is not limited to polychromic X-rays in only two colors. More colors may be used.

The present invention may also include a scintillator screen positioned adjacent to the mask. The scintillator screen includes a plurality of different scintillator materials, with the different scintillator materials emitting electromagnetic radiation at different wavelengths. For example, the first scintillator material may emit first wavelengths of visible light when absorbing X-rays of a first energy level, and the second scintillator material may emit second wavelengths of visible light when absorbing X-rays of a second energy level. The mask may be a color filter grid. The scintillator screen may be positioned against the mask, or spaced apart from the mask.

In one embodiment, the present invention provides a radiography system, having: a radiography sensor pad; and a mask disposed across the radiography sensor pad. The mask comprises a repeating pattern of first and second portions, wherein the first portions are configured to pass first wavelengths of X-rays therethrough, and the second portions are configured to pass second wavelengths of X-rays therethrough. In preferred embodiments, the mask is formed directly onto an image-receiving surface of the radiography sensor pad. The mask may be formed by material deposition (e.g.: copper deposition) onto the image-receiving surface of the radiography sensor pad. Most preferably, the material (which may be copper, but need not be so) is deposited so as to form a repeating pattern of rectangular sections (leaving openings therebetween) on the image-receiving surface of the radiography sensor pad. In preferred embodiments, this will give the image-receiving surface a "grid" or "checkerboard" appearance.

The present invention operates by allowing a first wavelength of X-rays to pass through the openings in the mask while simultaneously allowing a second wavelength of X-rays to pass through the sections of material deposits in the mask.

Most preferably, the repeating pattern of material deposits and openings therebetween is dimensioned small enough such that each opening or material deposit covers only a few pixels of the radiography sensor pad. As a result, a single X-ray directed at the radiography sensor pad can be recorded as a first image (corresponding to the first wavelength of light passing through the openings in the mask) and a second image (corresponding to the second wavelength of light passing through the material depositions in the mask).

The present invention also provides a method of taking a polychromic X-ray, by: passing an X-ray beam through a body part, and through a mask disposed across a radiography sensor pad, and onto the radiography sensor pad, wherein the mask comprises a repeating pattern of first and second portions, wherein the first portions are configured to pass first wavelengths of electromagnetic radiation therethrough, and the second portions are configured to pass second wavelengths of electromagnetic radiation therethrough, thereby taking a first image corresponding to the first wavelengths of electromagnetic radiation; thereby taking a second image corresponding to the second wavelengths of electromagnetic radiation; and comparing the first and second images to generate a polychromic X-ray image.

The present invention also provides a method of configuring a radiography sensor pad for taking polychromic X-ray images, by: depositing a repeating pattern of material onto the image-receiving surface of the radiography sensor pad, wherein openings between the material permit first wavelengths of X-rays to pass therethrough, and wherein the material permits second wavelengths of X-rays to pass therethrough.

DETAILED DESCRIPTION OF THE FIGURES

Figure 1:
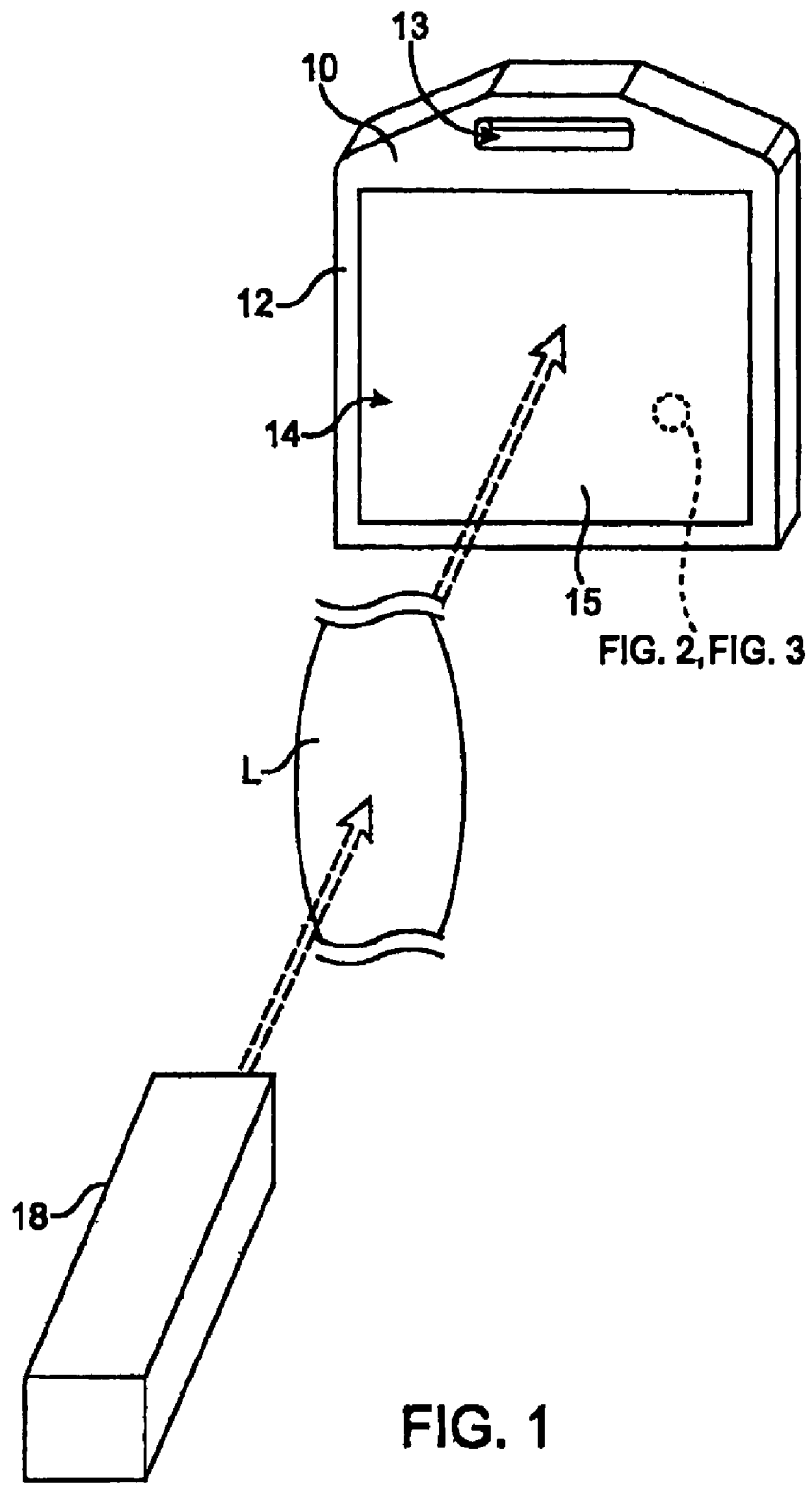
FIG. 1 is a perspective view of a first embodiment of the present invention in operation.
Figure 2:
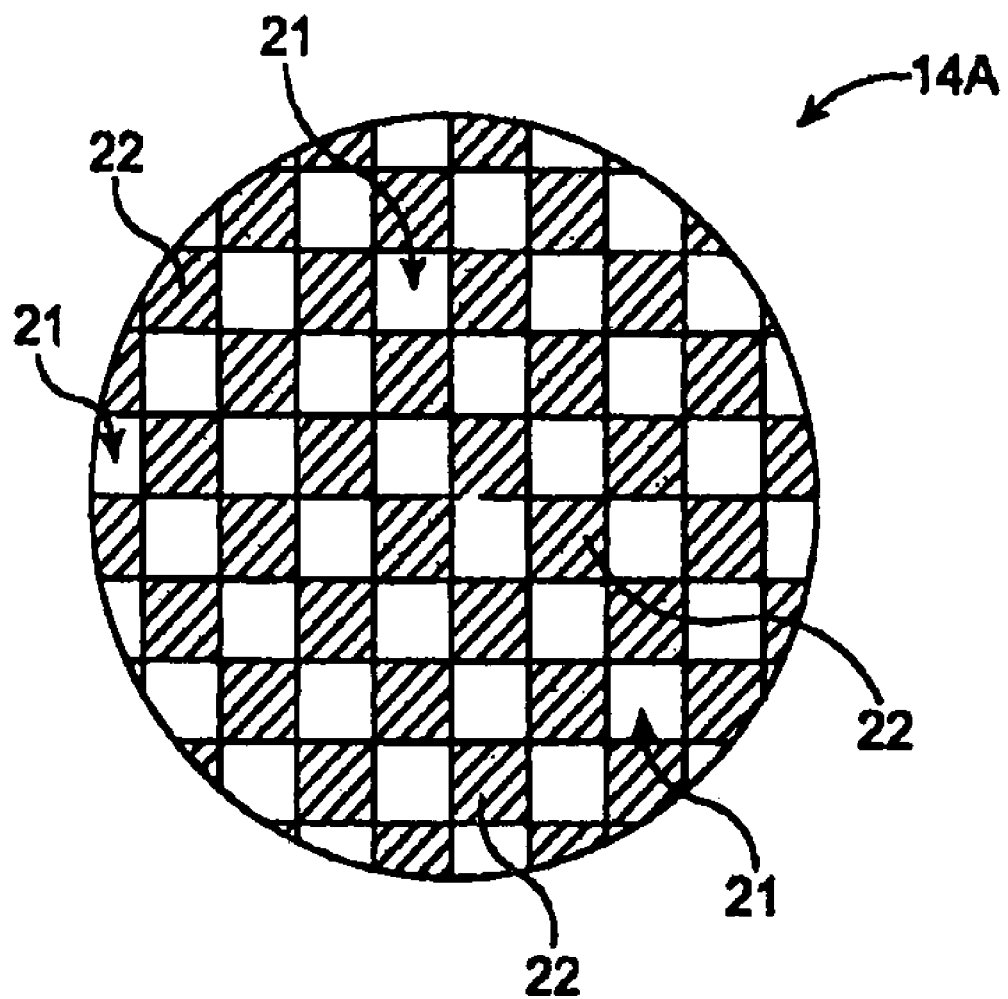
FIG. 2 is an enlarged view of a first embodiment of the image receiving surface of a digital radiography sensor pad (corresponding to the dotted line section shown in FIG. 1).
Figure 3:
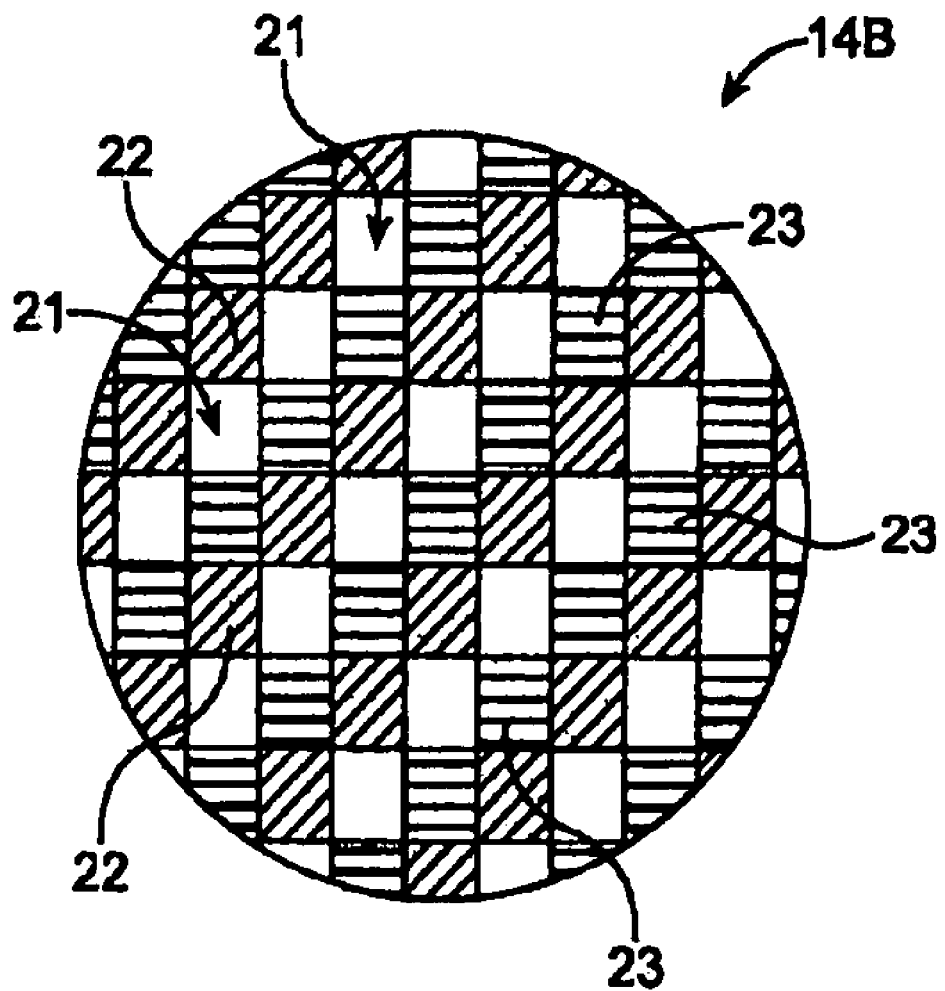
FIG. 3 is an enlarged view of a second embodiment of the image receiving surface of a digital radiography sensor pad corresponding (corresponding to the dotted line section shown in FIG. 1).
Figure 4:
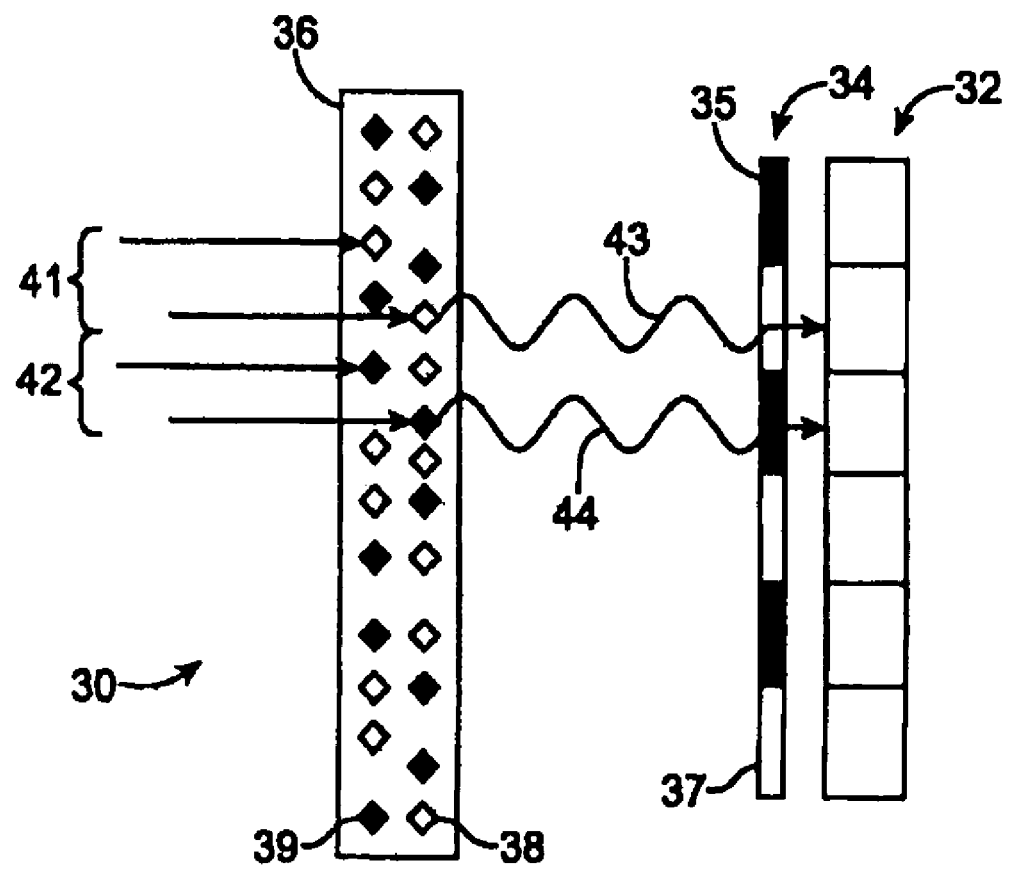
FIG. 4 is a schematic side elevation view of a second embodiment of the invention, showing a scintillator screen, a mask and a pixiliated detector.
Figure 6:
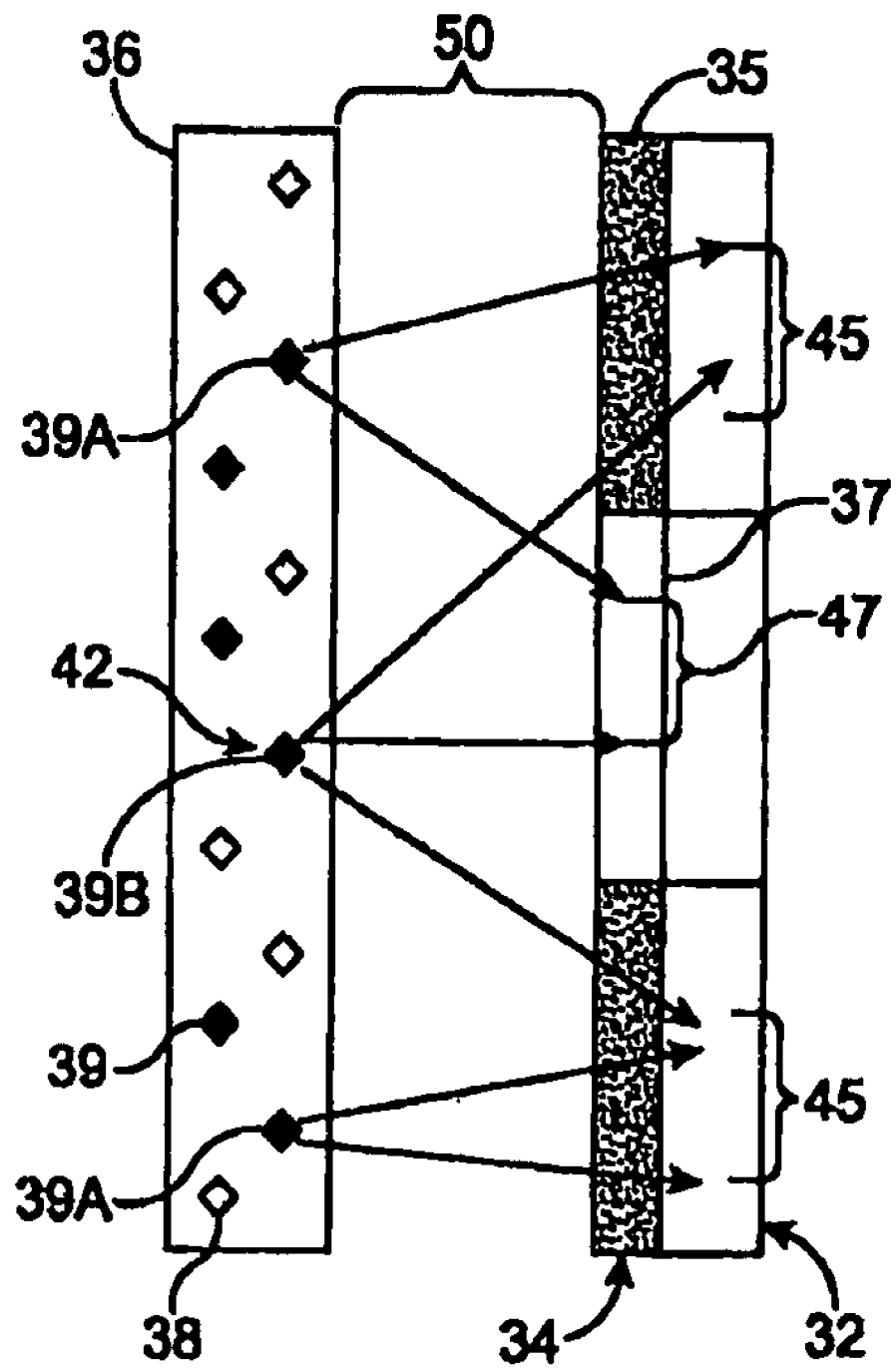
FIG. 6 is a view similar to FIGS. 4 and 5, but with the scintillator screen spaced apart from the mask.
Figure 7:
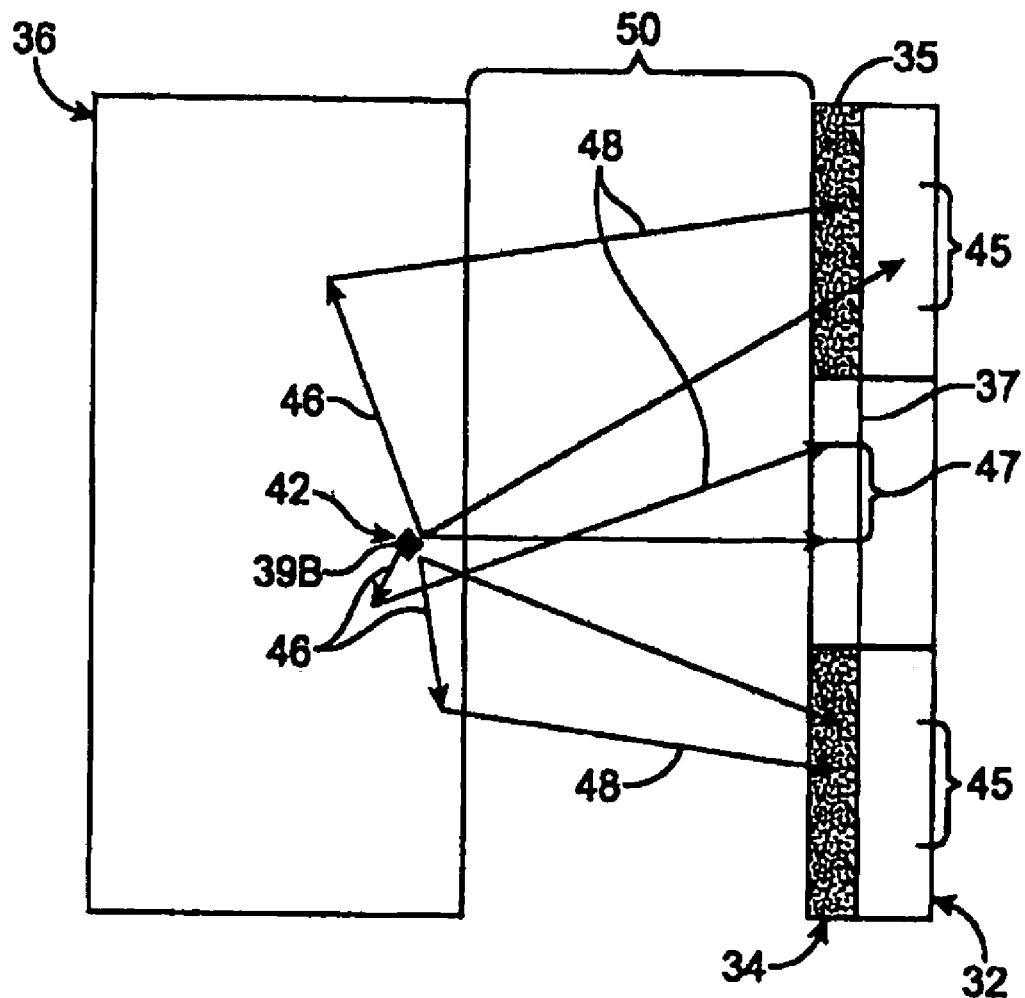
FIG. 7 is a view similar to FIG. 6, showing the effects of scattering.
Figure 8:
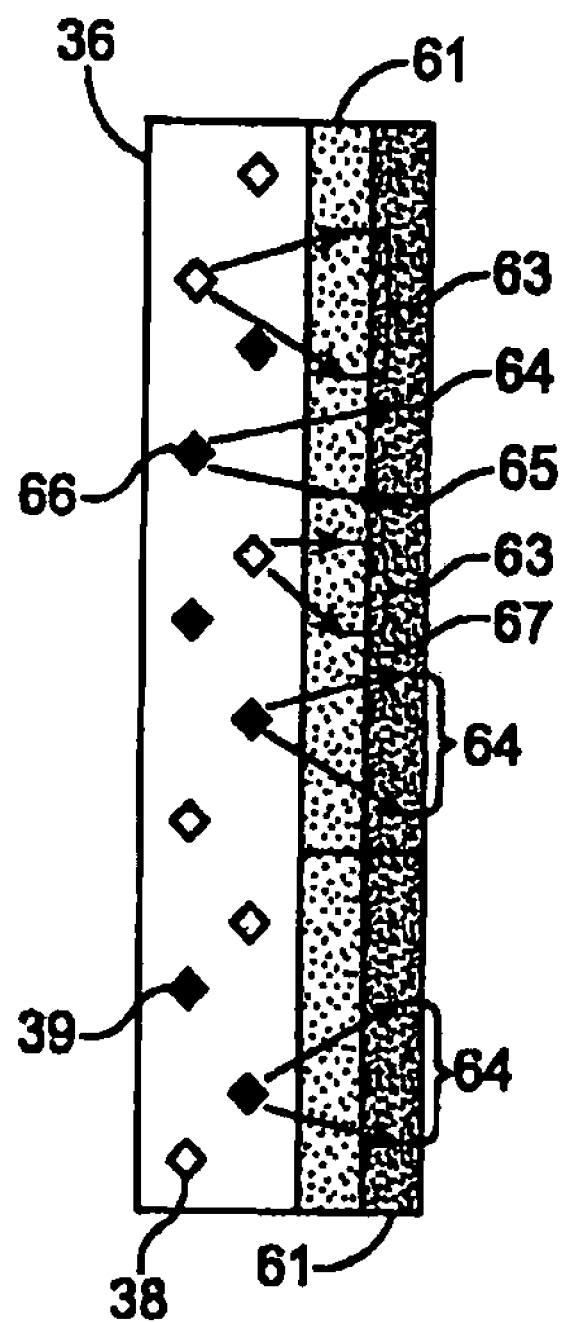
FIG. 8 is schematic side elevation view of a third embodiment of the invention, showing a scintillator screen; and a pixiliated detector formed by two layers of materials, each being configured to pass different wavelengths of electromagnetic radiation therethrough.

FIGS. 1 to 3 show a first embodiment of the present invention; FIGS. 4 to 7 show a second embodiment of the present invention; and FIG. 8 shows a third embodiment of the present invention.

Referring to FIG. 1, the present invention provides a radiography system 10, comprising: a radiography sensor pad 12 with a mask 14 disposed thereon. Radiography sensor pad 12 is configured to receive an X-ray image of a body part (e.g.: a patient's leg, L) when used with an X-ray emitter 18. In various embodiments, radiography sensor pad 12 may be portable and handheld (e.g.: having handle 13, as shown). It is to be understood, however, that radiography sensor pad 12 need not be portable at all. Moreover, keeping within the scope of the present invention, radiography sensor pad 12 may comprise any standard commercially available radiography sensor pad, and is not limited to any particular radiography sensor pad.

Radiography sensor pad 12 includes an image receiving surface 15 that is preferably digital (i.e.: pixilated) for reasons that will be explained.

In accordance with the present invention, a "mask" 14 is applied onto image receiving surface 15. Two different embodiments are shown of mask 14 in FIGS. 2 and 3, respectively.

Referring first to FIG. 2, mask 14A comprises a repeating pattern of first and second portions, 21 and 22. First portion 21 may simply comprise an opening through mask 14A. Second portion 22 may simply comprise a region where a material is deposited directly onto image receiving surface 15 of radiography sensor pad 12.

In one embodiment, mask 14 is simply formed by deposition of (small) copper sections (i.e.: portions 22) onto image-receiving surface 15 of radiography sensor pad 12. The present invention is not limited to copper deposition, other materials may be used as well.

As can be seen, copper sections 22 are preferably rectangular in shape and of the same size as openings 21 therebetween. This gives mask 14 its illustrated "checkerboard" or "grid" appearance.

In accordance with the present invention, a first wavelength of light passes through openings 21 (i.e.: the full wavelength of light emitted by X-ray emitter 18). However, the regions where copper is deposited on image-receiving surface 15 (i.e.: portions 22) will not permit the full wavelength (or wavelength range) of light emitted by X-ray emitter 18 to pass through. Instead, only a second wavelength (or wavelength range) of light will pass through portions 22.

In preferred embodiments, regions 21 and 22 of mask 14 are very small. Most preferably, individual regions 21 and 22 only overlay one (or a few) pixels of image-receiving surface 15. For example, in preferred embodiments, each of the individual first and second portions 21 and 22 of mask 14 covers one or more individual pixels of the radiography sensor pad. As a result, the single X-ray beam emitted by emitter 18 can be used to simultaneously produce two X-ray images. Specifically, the first X-ray image will correspond to the image received by the pixels in openings 21; and the second X-ray image will correspond to the image received by the pixels behind the copper depositions in regions 22.

In accordance with a second embodiment of mask 14, a repeating pattern having more than two types of regions is provided. For example, as shown in FIG. 3, regions 21 and 22 remain as explained above. In addition, however, a plurality of third portions 23 are also provided. Portions 23 may comprise locations where a material other than that used in regions 22 is deposited. Or, portions 23 may comprise the same material deposited in regions 22, but at different thicknesses). As a result, a first wavelength (or range of wavelengths) of light passes through openings 21 while other wavelengths (or range of wavelengths) of light pass through each of regions 22 and 23. Thus, three different (e.g.: polychromic) images can be extracted from a single X-ray beam from emitter 18.

It is to be understood that although mask 14 is preferably formed directly onto image-receiving surface 15 of the radiography sensor pad 12, it need not be so. For example, mask 14 may be spaced a (small) distance away from image-receiving surface 15 (similar to the embodiment shown in FIG. 6).

The present invention also provides a method of taking a polychromic X-ray, by: passing an X-ray beam through a body part (e.g.: leg L), and then through mask 14 disposed across a radiography sensor pad 12, and then onto radiography sensor pad 12. Thereafter, a first image is generated corresponding to first wavelengths of X-rays passing through regions 21. A second image is also generated, corresponding to the second wavelengths of X-rays passing through regions 22. Thereafter, the first and second images are compared to generate a polychromic X-ray image.

The present invention also provides a method of configuring a radiography sensor pad 12 for taking polychromic X-ray images, by: depositing a repeating pattern of material (e.g.: regions 22) onto image-receiving surface 15 of radiography sensor pad 12, wherein openings 21 between regions 22 first wavelengths of X-rays to pass therethrough, and wherein the material deposited in regions 22 permit second wavelengths of X-rays to pass therethrough.

FIGS. 4 to 7 show a second embodiment of the invention in which digital radiography system 30 includes a pixilated optical detector 32, and a mask 34 positioned adjacent thereto. Mask 34 includes a repeating pattern of first and second portions 35 and 37 configured to pass different wavelengths of electromagnetic radiation therethrough. In preferred embodiments, first and second portions 35 and 37 of mask 34 pass different wavelengths of X-rays or visible light therethrough.

First and second portions 35 and 37 of mask 34 are preferably formed as a grid, similar to the grid shown in FIGS. 2 and 3. In optional embodiments, a repeating pattern of third portions may also be included (in a manner similar to that shown in FIG. 3) may also be included. In such embodiments, the third portions are configured to pass wavelengths of electromagnetic radiation therethrough that are different from the wavelengths of electromagnetic radiation passing through the first and second portions 35 and 37 of mask 34.

Figure 5:
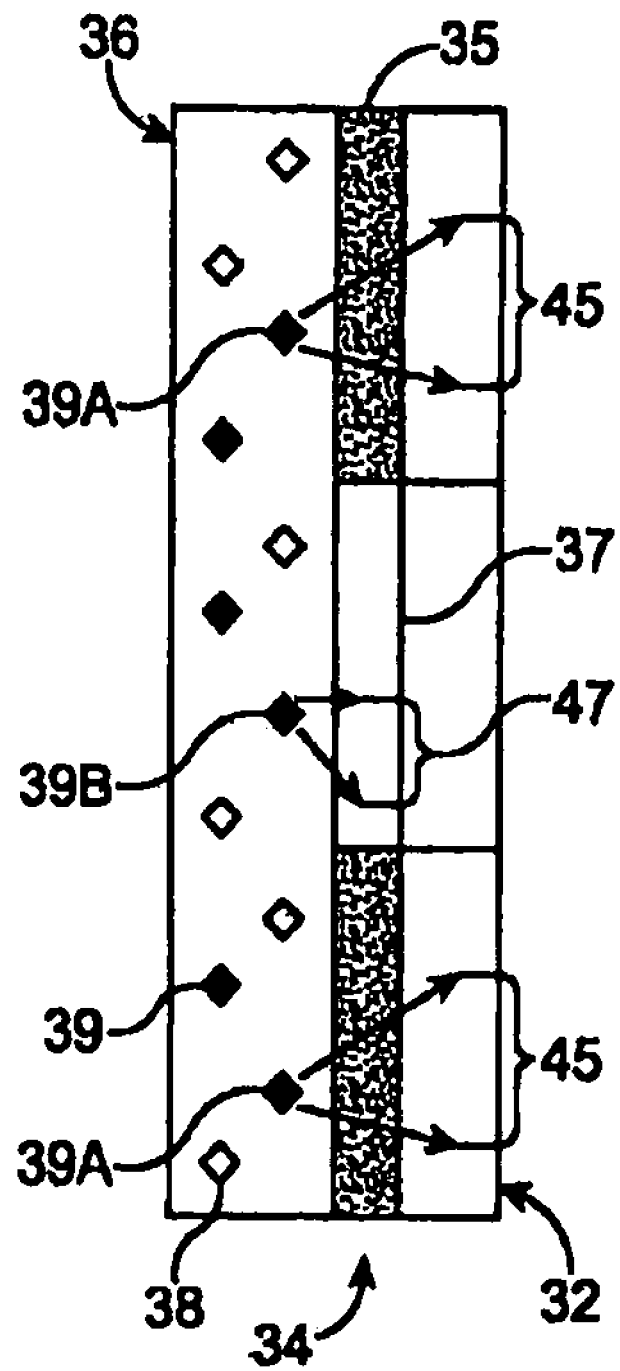
FIG. 5 is a view similar to FIG. 4, but with the scintillator screen, mask and pixiliated detector positioned against one another.

Radiography system 30 preferably also includes a scintillator screen 36 positioned adjacent to mask 34. As will be explained, scintillator screen 36 may either be positioned against mask 34 (as shown in FIG. 5), or positioned spaced apart from mask 34 (as shown in FIGS. 6 and 7). As will be explained, an advantage of the present invention is that substantially all of the optical photons emitted by scintillator screen 36 impinge upon optical detector 32. This avoids the quantum sink and low detective quantum efficiency problems of pre-existing systems.

Scintillator screen 36 preferably is made from a mixture of different types of grains of scintillator. For example, grains 38 are sensitive to low-energy X-rays 41, and grains 39 are sensitive to high-energy X-rays 43. Scintillator grains 38 and 39 emit different colors of optical photons (visible light) for each absorbed X-ray photon. IE: scintillator grains 38 emit a first color 43 of visible light, whereas scintillator grains 39 emit a second color 44 of visible light. The color of visible light 43 is different from the color of visible light 44. Thus, first scintillator grain material 38 emits first wavelengths of visible light when absorbing X-rays of a first energy level, and second scintillator grain material 39 emits second wavelengths of visible light when absorbing X-rays of a second energy level.

Mask 34 is a color filter array with first regions 35 transmitting light of color 44 therethrough and second regions 37 transmitting light of color 42 therethrough. The optical photons transmitted by the color filter array impinge upon, and are recorded by, a pixilated optical detector 32.

In preferred embodiments, the first and second regions 35 and 37 of mask 34 are very small. Most preferably, individual first and second regions 35 and 37 of mask 34 only overlay one (or a few) pixels of image-receiving optical detector 32.

As a result, a single X-ray beam (having a low energy component 41 and a high energy component 42 can be used to simultaneously produce two X-ray images. Specifically, the first X-ray image will correspond to the image received by the pixels in optical detector 10 behind portions 37 of mask 34, whereas the second X-ray image will correspond to the image received by the pixels in optical detector 32 behind portions 35 of mask 34.

The present invention also provides a method of taking a polychromic X-ray, by: passing an X-ray beam through a body part (e.g.: leg L in FIG. 1), and then through mask 14 or 34 disposed across a radiography sensor pad 12 or optical detector 32. Thereafter, a first image is generated corresponding to first wavelengths of X-rays passing through regions 21 or 35. A second image is also generated, corresponding to the second wavelengths of X-rays passing through regions 22 or 37. Thereafter, the first and second images are compared to generate a polychromic X-ray image.

FIGS. 1 to 7 all show a method of taking a polychromic X-ray, by: passing an X-ray beam through a body part, and through a mask 14 or 34 disposed across an optical detector 10 or 32, wherein mask 34 comprises a repeating pattern of first and second portions (21 and 22) or (35 and 37), wherein the first portions are configured to pass first wavelengths of electromagnetic radiation therethrough, and the second portions are configured to pass second wavelengths of electromagnetic radiation therethrough, generating a first image corresponding to the first wavelengths of electromagnetic radiation; generating a second image corresponding to the second wavelengths of electromagnetic radiation; and comparing the first and second images to generate a polychromic X-ray image.

FIG. 5 illustrates some details of one embodiment of the invention. In this case, the scintillator screen 36 is placed directly adjacent to the color filter array (mask) 34, which is directly adjacent to pixilated detector 32. Considering just the high-energy-sensitive scintillator grains 39, some grains 39A lie near first portions 35 of the optical filter mask 34, in which case the optical photons 45 emitted pass through first portions 35 of mask 34 and are detected in the pixilated detector 32. On the other hand, some grains 39B lie near second portions 37 of mask 34, in which case the optical photons 47 emitted are absorbed by mask 34 and are not detected by the pixilated detector 10. The emitted optical photons 47 of grains 39B that are not detected represent a fundamental degradation of the performance of the system. These grains 39B absorb X-ray photons that are never detected as part of the image, a situation referred to as a quantum sink. The same condition applies correspondingly to the low-energy-sensitive grains 38.

FIG. 6 illustrates another embodiment of the invention. In this case, the scintillator screen 36, is spaced a distance 50 away from the color filter array mask 34, which is directly adjacent to pixilated detector 10. In this case, the optical photons emitted from all grains are able to spread laterally before they reach the color filter 34. Thus, all grains 39A and 39B emit some optical photons 47 that fall on second regions 37 and are absorbed and not detected, and emit other optical photons 45 that fall on first regions 35 and are detected. Again, the same condition applies correspondingly to the low-energy-sensitive grains 38. Importantly, no grain is precluded from having its optical emission detected, and therefore no absorbed X-ray is precluded from being detected as part of the image. Thus, there is no quantum sink.

In addition, some grains 39B emit optical photons 45 that are detected in detector pixels laterally displaced with respect to the grain 39B. The effect of this is blurring of the image. The larger the spacing between scintillator screen 36 and the combination of color filter mask 34 and pixilated detector 32, the greater will be the blurring effect.

Optical scattering within the scintillator screen 36 also contributes to blurring as illustrated in FIG. 7 where some of the optical photons 46 are scattered 48 such that they arrive at adjacent color filters (i.e.: first and second regions 35 and 37). The effect that blurring has of removing the quantum sink does not depend on whether the blur is caused by scatter in the X-ray sensitive layer 36, or by spreading caused by the spacing 50 between scintillator screen 36 and color filter mask 34. Therefore, a preferred embodiment of the invention may include a system wherein the lateral size of first and second regions 35 and 37 (and therefore of the pixels in detector 10) is small compared to the blur caused by scatter in the X-ray-sensitive layer 36. In such an embodiment, the preferred spacing 50 tends toward zero. However, one may choose to use a larger size of first and second regions 35 and 37, if the desire is to reduce the number of detector pixels, for example to reduce cost.

A color filter mask 34 with more than two types of color responses may be used. The only requirement is that the optical emissions from the two types of scintillator grains 38 and 39 be distinguishable; for example, by forming linear combinations of the output of the detectors corresponding to the more than two types of color responses. In addition, more than two types of scintillator grains may be used, in which case at least as many types of filter regions would be needed. The color responses of the types of filter regions would be chosen such that optical emissions of each of the types of scintillators would be distinguishable.

FIG. 8 shows a third embodiment of the digital radiography system, including: scintillator screen 36; and a pixilated optical detector 32 positioned adjacent to scintillator screen 36. Pixilated optical detector 32 has first and second layers 61 and 61 of materials, being configured to pass different wavelengths of electromagnetic radiation therethrough. Scintillator screen 36 is formed from a plurality of different scintillator materials, the different scintillator materials each configured to emit electromagnetic radiation at different wavelengths, as was described above.

As seen in FIG. 8, the color sensitivity is not created by color filter regions that are laterally adjacent to one another, but rather have multiple optical detector layers 61 and 62 that are sensitive to different colors. Specifically, a first optical detector layer 61 is preferentially sensitive to a first color, and a second layer 62 is preferentially sensitive to a second color. Incident optical photons of the first color 63 are absorbed in the first layer 61, and optical photons of the second color 64 pass through the first layer 61 and are absorbed in the second layer 62. It is to be understood that more than two optical detector layers may be utilized so long as the optical photons 63 emitted from low-energy-sensitive grains 38 are distinguishable from the optical photons 64 emitted from high-energy-sensitive grains 39 as previously described. Also, as described above, more that two types of scintillator grains may be used having different X-ray energy sensitivities and different optical emission colors. Exemplary optical image detectors such as those described in Infrared Technology and Applications XXIX. Edited by Andresen, Bjorn F.; Fulop, Gabor F. Proceedings of the SPIE, Volume 5074, pp. 318-331 (2003).}, Gilblom, D. L., Yoo, S. K., Ventura, P. may be used in this embodiment of the invention.

Considering high-energy grains 66 as an example, some optical photons 65 emitted from some high-energy sensitive grains 66 may be recorded in image pixels 67 laterally displaced with respect to the grain 66. This is a blurring mechanism analogous to those described above. In addition, the blurring mechanism of optical scatter described above would normally be expected to be present. These same arguments apply correspondingly to low-energy-sensitive grains 38. Additionally, blurring is not required to overcome the optical quantum sink described in the other embodiments. Thus, the pixel size of the optical detector can be chosen entirely for convenience.

What is claimed is:

1. A radiography system, comprising: a radiography sensor pad; and a mask disposed across the radiography sensor pad, wherein the mask comprises a repeating pattern of first and second portions, wherein the first portions are configured to pass first wavelengths of electromagnetic radiation therethrough, and the second portions are configured to pass second wavelengths of electromagnetic radiation therethrough, wherein the mask further comprises: a plurality of third portions, wherein the mask comprises a repeating pattern of first, second and third portions, and wherein the third portions are configured to pass third wavelengths of electromagnetic radiation therethrough.

2. A method of taking a polychromic radiograph, comprising: passing electromagnetic radiation through an object, a scintillator screen and through a mask disposed across an optical detector, and onto the optical detector, wherein the mask comprises a repeating pattern of first and second portions, wherein the first portions are configured to pass first wavelengths of electromagnetic radiation therethrough, and the second portions are configured to pass second wavelengths of electromagnetic radiation therethrough, and wherein the scintillator screen comprises a plurality of scintillator materials configured to emit electromagnetic radiation at different wavelengths, generating a first image corresponding to the first wavelengths of electromagnetic radiation; generating a second image corresponding to the second wavelengths of electromagnetic radiation; and comparing the first and second images to generate a polychromic digital radiograph image.

3. The method of claim 2, wherein passing the electromagnetic beam through the mask comprises: passing the first wavelengths of electromagnetic radiation through openings in the mask, and passing the second wavelengths of electromagnetic radiation through material deposited on an image-receiving surface of the optical detector.

4. A radiography system, comprising: a pixilated optical detector; and a mask positioned adjacent to the pixilated optical detector, the mask comprising a repeating pattern of first and second portions configured to pass different wavelengths of electromagnetic radiation therethrough, wherein the mask further comprises a repeating pattern of third portions, the third portions being configured to pass wavelengths of electromagnetic radiation therethrough that are different from the wavelengths of electromagnetic radiation passing through the first and second portions of the mask.

5. A radiography system, comprising: a pixilated optical detector; and a mask positioned adjacent to the pixilated optical detector, the mask comprising a repeating pattern of first and second portions configured to pass different wavelengths of electromagnetic radiation therethrough, further comprising: a scintillator screen positioned on the same side of both the first and second portions of the mask, wherein the scintillator screen is positioned spaced apart from the mask.

6. A radiography system, comprising: a pixilated optical detector; and a mask positioned adjacent to the pixilated optical detector, the mask comprising a repeating pattern of first and second portions configured to pass different wavelengths of electromagnetic radiation therethrough; and a scintillator screen, wherein the scintillator screen comprises a plurality of different scintillator materials, the different scintillator materials each configured to emit electromagnetic radiation at different wavelengths.

7. The radiography system of claim 6, wherein the mask is formed directly onto an image-receiving surface of the optical detector.

8. The radiography system of claim 7, wherein the mask is formed by material deposition onto the image-receiving surface of the optical detector.

9. The radiography system of claim 7, wherein the mask is formed as a grid on the image-receiving surface of the optical detector.

10. The radiography system of claim 6, wherein the first portions are openings in the mask.

11. The radiography system of claim 10, wherein the second portions are material disposed on the optical detector.

12. The system of claim 6, wherein the first and second portions of the mask are configured to pass different wavelengths of visible light therethrough.

13. The system of claim 6, wherein the repeating pattern of first and second portions configured to pass different wavelengths of electromagnetic radiation therethrough is a grid.

14. The system of claim 6, wherein the plurality of different scintillator materials comprise first and second scintillator materials, and wherein the first scintillator material emits first wavelengths of visible light and the second scintillator material emits second wavelengths of visible light.

15. The system of claim 6, wherein a first scintillator material emits first wavelengths of visible light when absorbing electromagnetic radiation of a first energy level, and a second scintillator material emits second wavelengths of electromagnetic radiation when absorbing electromagnetic radiation of a second energy level.

16. The system of claim 6, wherein the mask is a color filter grid.

17. A radiography system, comprising: a scintillator screen; and a pixilated optical detector positioned adjacent to the scintillator screen, the pixilated optical detector comprising first and second layers of materials, the first and second layers of materials being configured to pass different wavelengths of electromagnetic radiation therethrough wherein the scintillator screen is positioned on the same side of both the first and second layers of materials.

18. A radiography system, comprising: a scintillator screen; and a pixilated optical detector positioned adjacent to the scintillator screen, the pixilated optical detector comprising first and second layers of materials, the first and second layers of materials being configured to pass different wavelengths of electromagnetic radiation therethrough, wherein the scintillator screen comprises a plurality of different scintillator materials, the different scintillator materials each configured to emit electromagnetic radiation at different wavelengths.

19. The radiography system of claim 18, wherein the first and second layers of the pixilated optical detector are positioned one on top of the other.

* * * * *